United States Patent [19]
Maxson et al.

[11] Patent Number: 5,137,520
[45] Date of Patent: Aug. 11, 1992

[54] CANNULA SKIRT

[76] Inventors: Wayne Maxson, 5465 Leitner Dr. W., Coral Springs, Fla. 33067; Stephen Chakoff, 15405 SW 72 Ct., Miami, Fla. 33157

[21] Appl. No.: 690,564

[22] Filed: Apr. 24, 1991

[51] Int. Cl.⁵ ............................................. A61M 25/02
[52] U.S. Cl. ................................ 604/180; 128/DIG. 26
[58] Field of Search ............... 604/174, 175, 177, 178, 604/179, 180; 128/916.26, 640

[56] References Cited

U.S. PATENT DOCUMENTS

| | | |
|---|---|---|
| 2,402,306 | 10/1943 | Turkel . |
| 2,898,917 | 4/1958 | Wallace . |
| 3,487,837 | 1/1970 | Petersen ................................ 604/180 |
| 3,568,679 | 11/1968 | Reif . |
| 3,683,911 | 8/1972 | McCormick . |
| 3,721,229 | 3/1973 | Panzer . |
| 3,856,020 | 12/1974 | Kovac . |
| 3,893,446 | 7/1975 | Miller . |
| 3,918,446 | 11/1975 | Buttaravoli ................. 128/DIG. 26 |
| 3,926,185 | 12/1975 | Krzewinski ................. 128/DIG. 26 |
| 4,170,995 | 10/1979 | Levine et al. . |
| 4,333,468 | 6/1982 | Geist ........................... 128/DIG. 26 |
| 4,380,234 | 4/1983 | Kamen . |
| 4,393,873 | 7/1983 | Nawash et al. . |
| 4,464,178 | 8/1984 | Dalton ............................ 604/180 |
| 4,516,968 | 5/1985 | Marshall et al. ............. 128/DIG. 26 |
| 4,519,793 | 5/1985 | Galindo .......................... 604/180 |
| 4,579,120 | 4/1986 | Mac Gregor ................... 604/180 |
| 4,593,681 | 6/1986 | Soni . |
| 4,645,492 | 2/1987 | Weeks . |
| 4,650,474 | 3/1987 | DeBacker . |
| 4,675,006 | 6/1987 | Hrushesky ....................... 604/180 |
| 4,717,385 | 1/1988 | Cameron et al. . |
| 4,767,411 | 8/1988 | Edmunds .......................... 604/180 |
| 4,915,694 | 4/1990 | Yamamoto et al. ............... 604/180 |

*Primary Examiner*—Paul J. Hirsch
*Attorney, Agent, or Firm*—Bacon & Thomas

[57] ABSTRACT

The present invention provides a device for immobilizing a cannula or sheath which is inserted into a patient's body in a laparoscopic surgical procedure. The device comprises a cannula skirt through which the cannula passes. The skirt contains a leakage cavity therein which is configured to minimize the pull-off forces which would tend to cause a separation of the skirt from the skin to which it is adhered during the surgical procedure. In addition, the leakage cavity provides enhanced flexibility to the cannula skirt so that the cannula can be angled during the procedure without causing excessive stress on the adhesive.

25 Claims, 4 Drawing Sheets

5,137,520

CANNULA SKIRT

FIELD OF THE INVENTION

The present invention relates to a surgical device for immobilizing or stabilizing a cannula or sheath through which a laparoscopic instrument or other instrument is inserted during surgery.

BACKGROUND OF THE INVENTION

Laparoscopic surgery (laparoscopy) is becoming a preferred method for performing various types of surgical opertions, particularly gynecological operations. However, unlike other types of surgical procedures, laparoscopic surgery does not require large incisions to expose the internal organs. Instead, a small hole is cut through the body wall and a laparoscope is inserted therethrough so that the surgeon can visualize the internal organs without the added trauma of a large incision. Various types of surgical instruments are also passed through these types of small holes so that the surgery can be performed while the organs are being visualized through the laparoscope. Thus, the surgery can be performed with a very small incision or hole through the body cavity which is about the diameter of the narrow instruments which are used during the surgical operation.

The instruments are not inserted directly through the hole in the body cavity. Instead, a tubular sheath or cannula is inserted through the hole and the instruments are passed through the opening in the sheath or cannula. Means may be provided for restraining the movement of the laparoscope within the cannula to minimize excessive movement of the laparoscope through the cannula. However, this does not prevent excessive movement of the cannula itself. Thus, the cannula may move up or down through the incision as the surgeon carries out the operation.

Movement of the cannula or sheath will cause undesirable movement of the laparoscope and this movement may distract the surgeon and interfere with the operation. Therefore, it is desirable to minimize the unwanted movement of the cannula. It is also desirable to restrict this unwanted movement of the cannula while allowing the surgeon to reposition the cannula as needed and to alter the angle of the cannula with respect to the patient's body without causing any unwanted up and down movement.

Various types of devices are available for restraining the movement of a cannula which passes into a patient's body. However, none of these devices are designed to overcome the unique problems associated with the requirements of laparoscopic surgery. For example, laparoscopic surgery requires distension of the body cavity by filling it with a fluid, especially $CO_2$ gas, under pressure, so that the instruments can be safely inserted and the organs can be visualized and manipulated during the operation.

Typically, devices which are designed to restrain or immobilize a cannula, have a clip or similar restraining means on an adhesive disk or pad which is adhered to the patient's skin at the point where the cannula enters the body. However, none of these devices are suitable for laparoscopic surgical procedures because of certain problems associated with the pressurized gas or other fluid in the body cavity. In particular, the pressurized $CO_2$ gas or fluid tends to be forced out through the incision and this leakage interferes with the adhesive which helps hold the cannula in place. Failure of the adhesive renders a restraining device useless once it becomes separated from the patient's skin. Furthermore, the amount of leakage increases once the cannula is no longer restrained by the adhesive pad over the incision. In addition, $CO_2$ gas tends to leak between the sheath and the laparoscopic device inserted therethrough.

Another problem associated with other types of prior art cannula stabilizers is that they are designed for use with cannulas which would not be suitable for use in a laparoscopic procedure. For example, cannulas which are in the form of thin flexible infusion or drainage tubes, would not be suitable in a laparoscopic procedure. Cannulas for use in a laparoscopic procedure are generally rigid and of a suitable diameter and length to accommodate the laparoscopic instrumentation. Therefore, the cannulas which are suitable for laparoscopic procedures cannot be bent around clips and similar devices since such bending and the like would make it impossible to insert the laparoscopic instrumentation into the body cavity.

One device for stabilizing the sheath of an endoscope is described in U.S. Pat. No. 4,593,681. The device includes a flexible plastic plate with a central hole through which the sheath of an endoscope passes. The hole is of a predetermined diameter to provide an interference fit with the sheath of a scope inserted therein. An adhesive is provided underneath the flexible plate to adhere the device on a person's body. However, no means is provided to lessen the strain on the adhesive due to the force of the fluid in the body cavity which tends to leak out during the procedure. In addition, this device requires a complex mechanism of moving parts to immobilize the sheath once it has been inserted within the central hole of the device. Furthermore, it is difficult to insert the cannula through the central hole of this device since no means is provided to enlarge the hole or otherwise open it up for easy passage of the cannula therethrough.

During a laparoscopic procedure, it is sometimes desirable to change the angle at which the cannula enters the body cavity in order to view different portions of the internal organs. However, this can place excessive stress on the adhesive and cause it to separate. Thus, it would be desirable to enhance the flexibility of a cannula restraining device so that the angle can be changed with a minimum of stress on the adhesive.

In view of the unique problems associated with stabilizing or immobilizing devices for use with laparoscopic instrumentation and the failure of others to solve these problems, it is clear that a long-felt need exists in the art to provide a device which can easily stabilize a laparoscopic cannula while avoiding the problems caused by the pressurized gas in the patient's body cavity.

SUMMARY OF THE INVENTION

It is an object of the present invention to provide a cannula skirt for stabilizing or restraining the movement of a laparoscopic cannula or sheath while minimizing the detrimental effects of $CO_2$ or fluid (liquid or gas) leakage on the adhesive seal between the device and the patient's skin.

It is also an object of this invention to enhance the flexibility of a device for restraining movement of a cannula so that the angle at which the cannula enters the body can be changed with a minimum of stress on the adhesive which holds the device to the patient's skin.

It is a further object to provide a method of conducting a laparoscopic or related surgical procedure which involves the use of a cannula or sheath through which the laparoscope or other instrumentation passes therethrough.

These and other objects are achieved by a stabilizing device in the form of a cannula skirt which has an improved design. In particular, the cannula skirt includes a specific leakage cavity and an air-leakage seal which improves the operation of the device when used in a laparoscopic or similar procedure. The skirt also incorporates a spring on top to enlarge the opening for the instrument to pass through and to then increase pressure on the cannula to minimize slippage or leakage.

The skirt is preferably made of flexible elastomeric material such as silicone rubber or similar plastic or rubber material which is used to make conventional medical devices such as tubes, cannulas, catheters, catheter supports or the like. The skirt has a central hole or passage through which a sheath or cannula is inserted. One end of the skirt may be widened to form a large flat surface with an adhesive on the bottom surface thereof. The adhesive, such as a pressure sensitive adhesive, permits the skirt to be adhered to the abdominal wall of the patient directly over the incision. The hole in the skirt may be sized to provide a snug fit (interference fit) to prevent excessive slippage of the sheath within the sleeve. The interference fit may be further enhanced by the use of a spring.

An air/liquid seal may be provided around the hole or passage. The seal is in the form of a stretchable/deformable lip around the circumference of the hole. The lip may be configured so that when a cannula is inserted through the hole in the sleeve, it stretches and deforms the lip which surrounds the cannula. As a result, the lip is forced against the cannula by its elasticity.

In addition, the bottom portion of the skirt includes a pressure leakage cavity which surrounds the air/liquid seal. The geometry of the cavity is designed to provide maximum flexibility of the skirt to allow great mobility of the laparoscope in the cannula without causing the unwanted movement of the cannula itself. Furthermore, the geometry of the leakage cavity is designed to transmit any pull-off forces to the center areas of the foot of the skirt and thereby maximize adhesion to the patient's skin.

BRIEF DESCRIPTION OF THE DRAWINGS

FIG. 5b is a top-view of the skirt shown in FIG. 5a;

FIG. 6b is a top view of the split cannula skirt shown in FIG. 6a;

DETAILED DESCRIPTION OF THE INVENTION AND PREFERRED EMBODIMENTS

Figure 1:
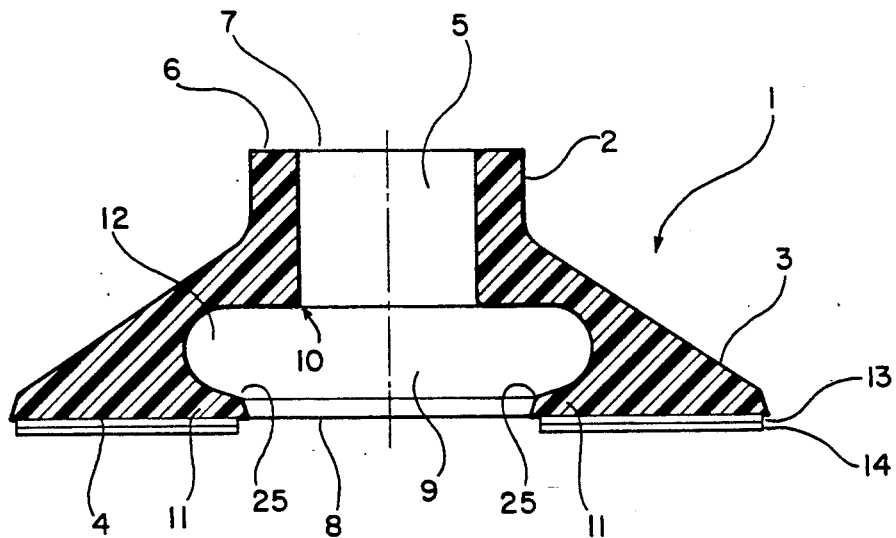
FIGS. 1, 2, 3 and 4 are cross-sectional view of different embodiments of the cannula skirt of the invention.

The cannula skirt of the present invention is particularly useful for stabilizing the cannula used in combination with a trocar such as the trocar/cannula assembly described in U.S. Pat. No. 4,601,710, the specification of which is incorporated herein by reference. An example of such a trocar/cannula assembly is available from U.S. Surgical Corporation and sold as the "Surgiport" 10 mm disposable surgical trocar.

The above-described device has a trocar for penetrating the body cavity and a cannula or sheath around the trocar. The trocar is removed from the assembly after the body cavity has been pierced so that the cannula or sheath is left in place. The cannula skirt of the present invention is used to stabilize the cannula or sheath which is left in place during the surgical procedure. It can be used in combination with any type of cannula or sheath which is designed to receive surgical instruments which are passed therethrough during a surgical operation.

The cannula skirt of the invention will now be described with reference to the drawings wherein like reference numerals designate like or corresponding elements throughout all the views and drawings.

FIG. 1 shows a cross-section of an embodiment of the invention which is a one piece molded skirt made out of flexible elastomeric material such as plastic, rubber of silicone. The skirt preferably includes a narrow stem segment 2 and a wider flanged section 3. In a preferred embodiment, the bottom 4 of the flanged section is substantially flat as shown in the figures. A passage, preferably tubular in cross section, extends from the top 6 to the bottom 4 of the skirt. The passage forms a top opening 7 and a bottom opening 8.

The passage includes an upper segment 5 which is sized to receive a cannula or sheath therethrough and a lower segment 9 which is wider than the upper segment. Preferably, the upper segment has a substantially constant cross-sectional diameter. The upper segment has a bottom portion 10 which is located where the two segments join each other. Thus, the upper segment of the passage extends from top opening 7 to the bottom portion 10 and the wider lower segment 9 extends from the bottom portion 10 to the bottom opening 8. Preferably the top and bottom openings are round.

In the preferred embodiment, the upper segment passes through the stem and the lower segment is contained in the flanged section of the skirt. Preferably, the flanged section is in a generally frusto conical shape wherein the base serves as the bottom. Also, in the preferred embodiment, the stem is cylindrical in shape and extends upward from the top of the frusto conical flanged section. Thus, in a preferred embodiment, the two segments of the passage, along with the top and bottom openings, are aligned with each other in a coaxial fashion to create a straight passage through the skirt.

The bottom of the skirt is configured to define the bottom opening 8 so that the diameter of the bottom opening is smaller than the diameter of the lower segment of the passage. This configuration provides a zone of constriction which forms a bottom wall 11 around the bottom of a lower segment so that the lower segment is partially enclosed to form the leakage cavity 12. Preferably, the diameter of the bottom opening is larger than the diameter of the upper segment of the passage so that fluid leaking out of the body cavity passes between the cannula and the circumference of the bottom opening and thereby enters the leakage cavity.

As shown in FIG. 1, a conventional pressure sensitive adhesive 13 is preferably coated onto the bottom 4 of the skirt. The adhesive is preferably covered by a conventional peel-away release sheet 14.

In a preferred embodiment, the diameter of the upper segment of the passage is sized to snugly fit the cannula or sheath. By a snug fit, it is meant that the diameter of the passage is sized to frictionally engage the cannula when a cannula is inserted therethrough so that the skirt provides some resistance when the cannula is pushed through the passage. As a result of the snug fit, the skirt can remain in a given location by frictional engagement with the cannula but can be manually moved along the cannula.

Figure 7:
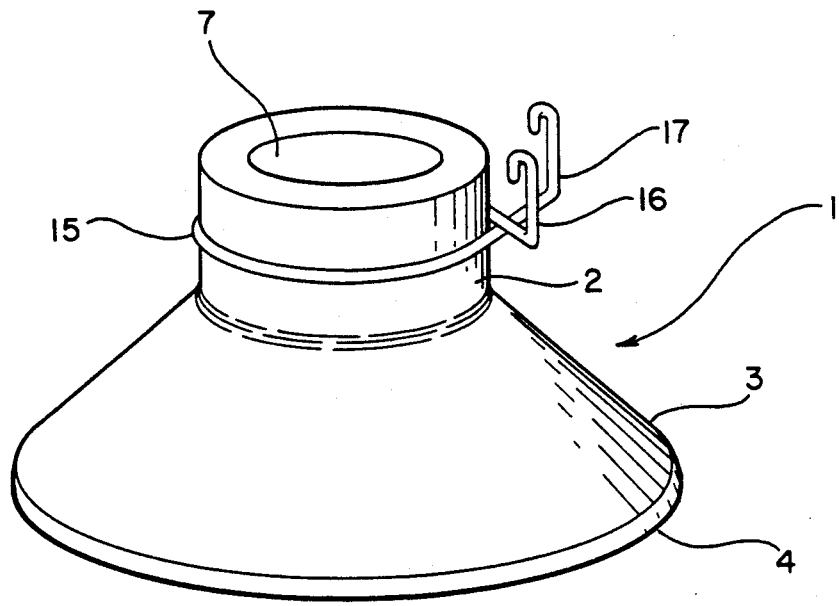
FIG. 7 is a perspective view of the cannula skirt of the invention shown with the torsional spring in place.
Figure 8:
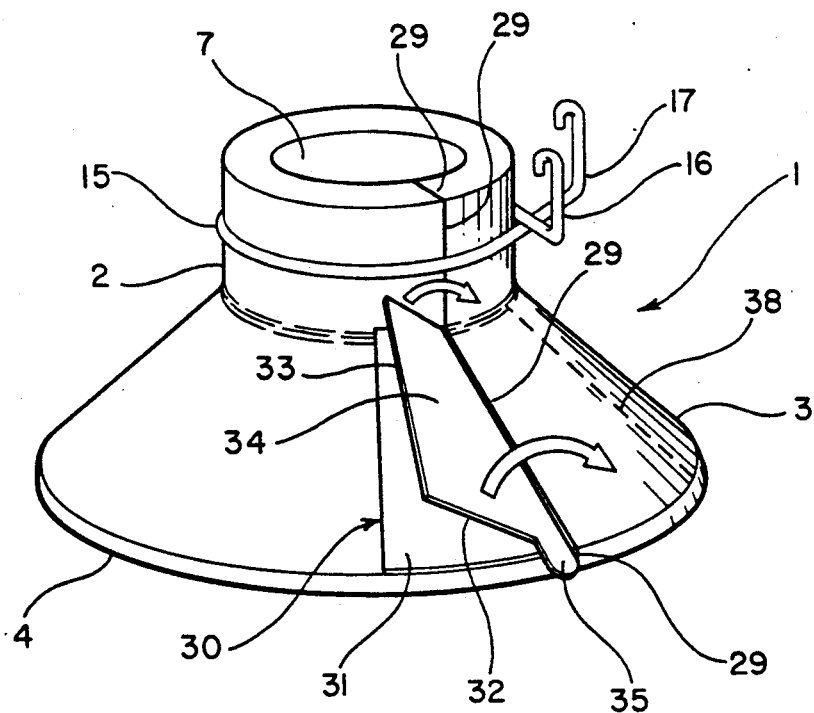
FIG. 8 is a perspective view of the cannula skirt of the invention shown with the torsional spring and adhesive strip in place.

The skirt of the invention is used to stabilize the cannula. In order to prevent movement of the cannula within the skirt, a torsional spring 15 may be attached to the skirt around stem 2 as shown in FIGS. 7 and 8. The tension of the spring is adjusted so that when the spring engages the stem, it constricts it to increase the friction between the cannula and the skirt. Thus, when a cannula is located within the passage and the torsional spring is frictionally engaged onto the stem, it becomes difficult for the cannula to move up or down through the passage of the skirt due to the constricting force of the torsional spring around the stem. This force can be removed by grasping the two upright members 16 and 17 with the thumb and forefinger and squeezing them together. This causes a reduction in the constriction and thereby allows the skirt to be moved up or down the cannula with relative ease.

Once the skirt is adhered to the patient's skin and the cannula has been positioned and locked into place by means of the torsional spring, then the cannula is relatively stable and cannot be easily moved up or down relative to the skirt. However, it will be apparent from the drawings 1 through 4 that the leakage cavity in the flanged section forms a substantial hollow volume within the skirt which serves to make the skirt more flexible. As a result of this flexibility, the cannula can be positioned along different angles without causing undue stress on the adhesive which binds the skirt to the patient's skin. This desirable feature exists regardless of whether gas or other fluid actually enters the leakage cavity, simply because the hollow area results in greater flexibility. Thus, one aspect of this invention pertains to the added flexibility of the skirt due to the hollow area in the flanged segment. The flexibility can be enhanced by making the upper surface of the flanged section concave as shown by the concave surface 23 in FIG. 3. A second aspect of the leakage cavity is related to its adaptation to receive liquid or gas, such as $CO_2$, which may leak through the incision during surgery. In prior art devices, gas/fluid which leaks through the incision has a tendency to cause the adhesive on the bottom of a stabilizing device to become separated from the patient's skin. This occurs because the leaking gas/fluid tends to push its way between the skin and the adhesive. This detrimental effect of leakage is minimized in the present invention due to the presence of the leakage cavity which is adapted to receive the gas/fluid leaking through the incision.

Figure 4:
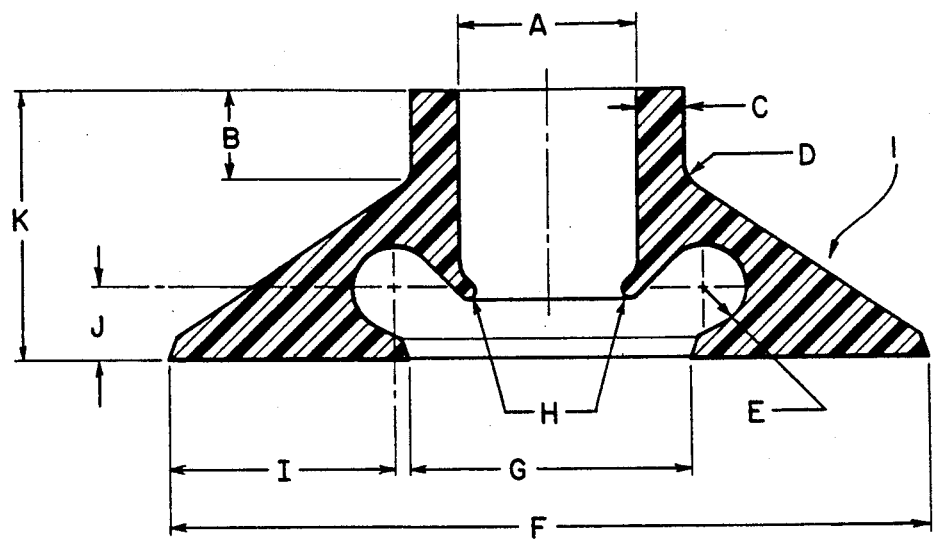
Figure 5B:
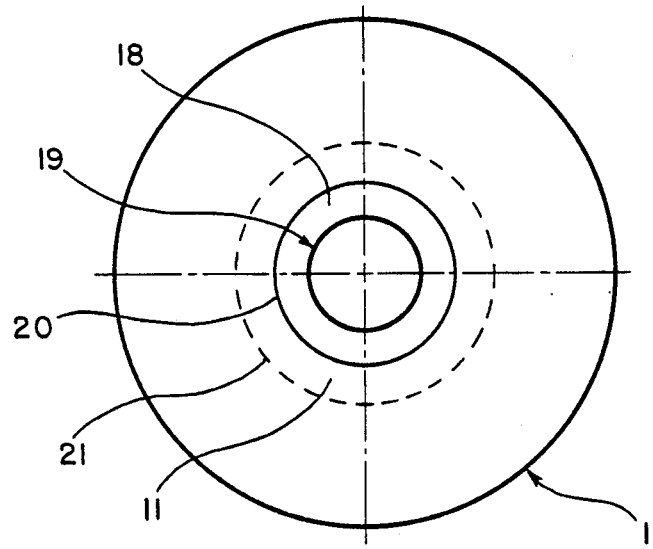
Figure 5A:
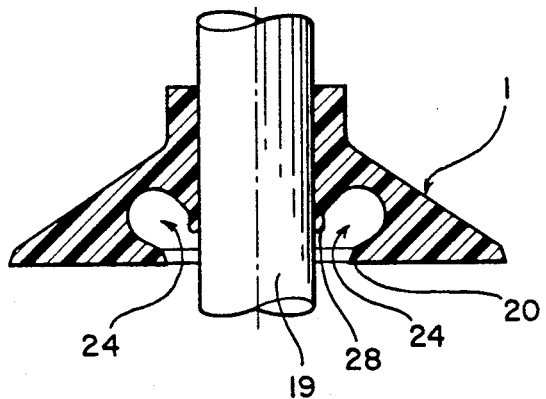
FIG. 5a is a cross-sectional view of the cannula skirt shown with a sheath or cannula inserted therethrough.

The leakage cavity is able to receive the gas/fluid which leaks through the incision by sizing the bottom hole so that it is wider than the diameter of the upper segment of the passage. Thus, the bottom opening 8 in FIGS. 1 through 4 with a diameter which is larger than the diameter of the upper segment of the passage. In this embodiment, the bottom opening is smaller than the diameter of the lower segment of the passage to partially enclose the lower segment and is wider than the diameter of the upper segment. Such an arrangement is shown in FIG. 5b which illustrates an annular zone 18 between the outside of cannula 19 and the circumference 20 of the bottom opening. Zone 18 is also illustrated in FIG. 5a which shows the direction of fluid flowing into the leakage cavity by arrow 24.

FIG. 5b also shows the zone of constriction forming the bottom wall 11 which partially encloses the lower segment to form the pressure leakage cavity. FIG. 5b shows the configuration of the lower segment of the passage by dash line 21. Thus, the zone of constriction 22 is shown in FIG. 5b as an annular zone between the circumference of circles 20 and 21.

When gas leaks into the pressure cavity 12, a force is exerted downward against the bottom wall 11. This force tends to minimize the pull-off forces which would be exerted against the adhesive if the pressure leakage cavity were not present. In the preferred embodiment, the leakage cavity has a curved cross-sectional configuration as shown by the curved wall 26. This curvature aids in minimizing the pull-off forces and thereby serves to further maximize adhesion to the patient's skin.

Figure 2:
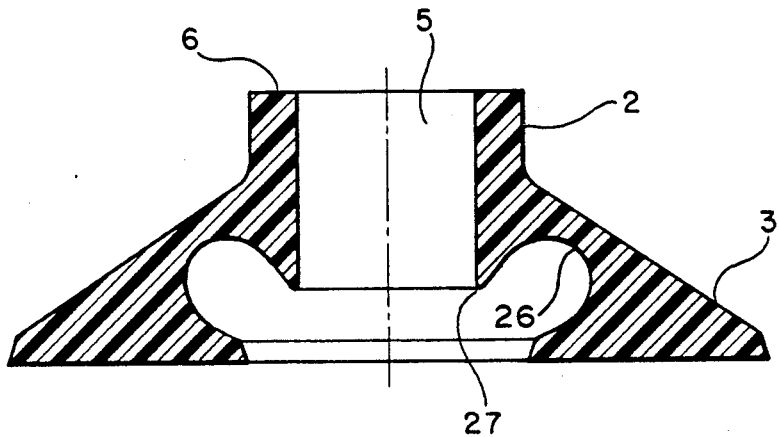
Figure 3:
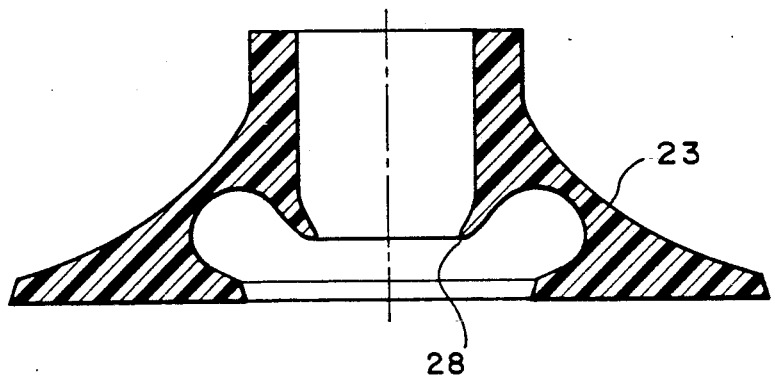
Figure 6B:
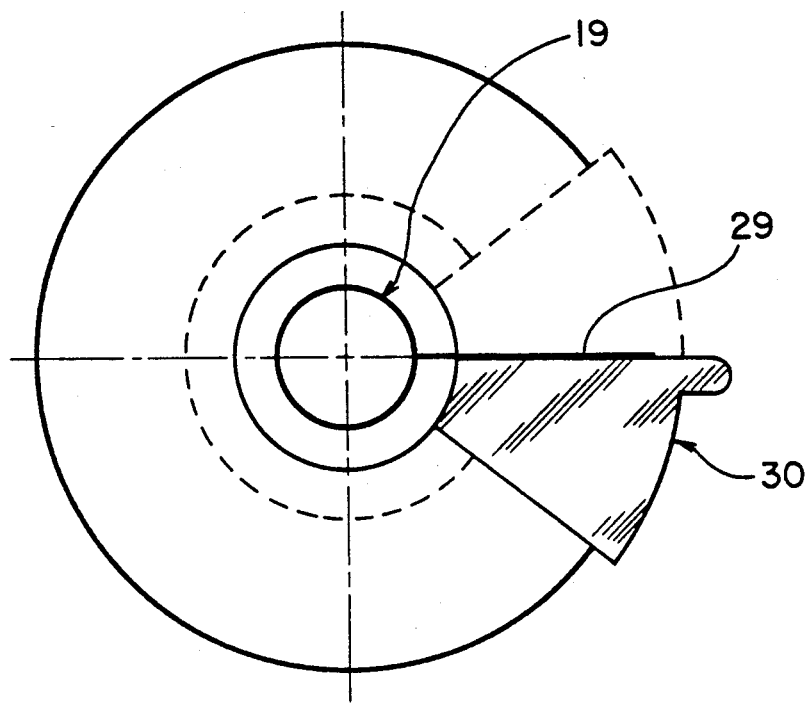
Figure 6A:
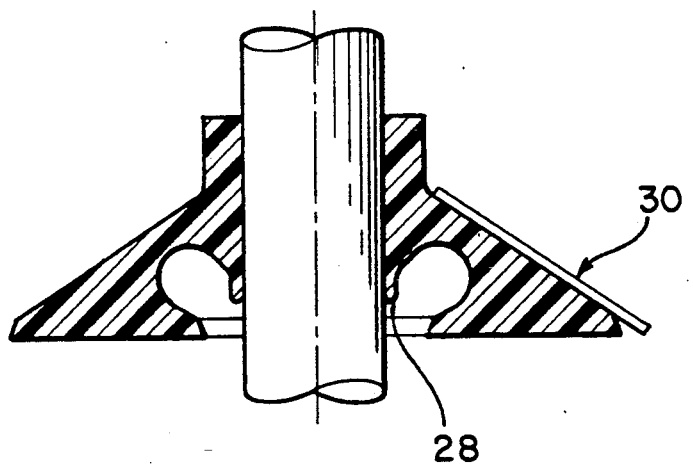
FIG. 6a is a cross-sectional view of a split cannula skirt embodiment of the invention with a sheath or cannula inserted therethrough.

In a preferred embodiment, a deformable lip is located around the bottom of the upper segment. In FIG. 2, a deformable lip 27 is shown which extends downward into the leakage cavity. Pressure in the cavity causes the lip to press against a cannula when a cannula is inserted through the skirt. The deformable lip may be configured to point downward and inward toward the center of the passage as shown in FIG. 3 by lip 28. The configuration of lip 28 results in a slight constriction around the bottom of the upper segment of the passage which results in a reduction of the diameter of the bottom of the upper segment. When a cannula is inserted through the skirt, the lip 28 is deformed as shown in FIGS. 5a and 6a. The resilience of various elastomeric materials such as silicone, plastic and rubber, causes the deformed lip to press against the cannula to enhance the seal.

In the embodiments shown in FIGS. 2 and 3, the leakage cavity is in a general annular configuration around the lip.

In another embodiment, the skirt is slit on one side so that the entire skirt can be opened up to make it easy for placing the skirt around a cannula. The slit skirt is shown in FIGS. 6a, 6b and 8. The slip 29 extends on one side of the skirt from the top to the bottom and passes through the thickness of the skirt to the passage. When the skirt is opened up along the slit, the cannula can be easily inserted through the open slit into the passage. The split skirt preferably includes an adhesive overlay which serves to keep the slit closed after the cannula has been inserted therethrough. The adhesive overlay is indicated in general by reference numeral 30 in FIGS. 6a, 6b and 8. One portion 31 of the adhesive overlay is adhered to the top of the flanged segment along one side of the slit. Another portion of the adhesive overlay forms a flap 32 along the side of the slit. The flap is coated with an adhesive 33 and release layer 34 is adhered to the adhesive coating. A tab 35 may be included on the release layer to aid in the removal of the release layer to expose the adhesive. In operation, the release layer is removed and the flap is bent down in the direction of the arrow shown in FIG. 8 to adhesively engage the top of the flange on the other side of the slit in the area between slit 29 and dash line 38. The portion of the slit on the stem is held in a closed position by the torsional spring 15.

The cannula skirt of this invention is used in a conventional laparoscopic procedure. Thus, the procedure includes inserting a cannula or sheath into a patient's body; stabilizing the cannula by adhering the skirt to the patient's skin with the cannula being inserted through the skirt. As a result of the design of the skirt and the use of a torsional spring therewith, the skirt is used without any adhesive in the passage to hold the cannula in place.

The skirt can be manufactured by conventional molding procedures to form a one-piece structure. However, although the skirt is preferably a one-piece molded article, it is possible to fabricate the skirt from a plurality of parts.

TABLE 1

| a. | 10.5 φ | g. | 15.5 φ |
|----|--------|----|--------|
| b. | 5.0    | h. | 0.5 R  |
| c. | 2.5    | i. | 12.4   |
| d. | 2.0 R  | j. | 3.9    |
| e. | 2.4 R  | k. | 15.0   |
| f. | 43.0 φ |    |        |

The skirt is ideally designed and dimensioned for use with any size cannula such as the "Surgiport" 10 mm disposable surgical trocar assembly sold by United States Surgical Corporation. An example of a skirt for use with a 10 mm cannula is shown in FIG. 4. The dimensions of the skirt are indicated by means of the letter designations a-k. The measurements in millimeters for each letter designation are shown below in Table 1 wherein φ refers to diameter and R refers to radius. The device shown in FIG. 4 can be scaled up or down to accommodate different size cannulas.

While the present invention has been described in terms of certain preferred embodiments and exemplified with respect thereto, one skilled in the art will readily appreciate that various modifications, changes, omissions and substitutions may be made without departing from the spirit thereof. It is intended therefore that the present invention be limited solely by scope of the following claims.

We claim:

1. A device for stabilizing a cannula or sheath, said device comprising a cannula skirt with a leakage cavity therein; said skirt having a top and a bottom with a passage extending from the top to the bottom to form a top opening and then contacting bottom opening; said passage having an upper segment with a diameter which is sized to receive a cannula or sheath therethrough, and a lower segment including said leakage cavity having a diameter which is greater than the diameter of the upper segment; and said bottom being configured to define the bottom opening having a smaller diameter than the diameter of the lower segment of the passage whereby said lower segment of the passage is partially enclosed by a bottom wall to form said leakage cavity.

2. The device of claim 1 wherein the diameter of the bottom opening is larger than the diameter of the upper segment of the passage.

3. The device of claim 2 wherein the bottom has a surface which is coated with an adhesive for securing said device to a patient's skin.

4. The device of claim 2 wherein the diameter of the upper segment of the passage is sized to snugly receive a cannula or sheath therethrough.

5. The device of claim 2 which further comprises a deformable lip around the circumference around the upper segment of the passage; said lip being capable of deforming to form a seal around a cannula or sheath when a cannula or sheath is inserted therethrough.

6. The device of claim 5 wherein the deformable lip is around the bottom of the upper segment adjacent to the lower segment of the passage whereby said lip is capable of pressing against a cannula or sheath when a cannula or sheath is inserted therethrough and the leakage cavity is under pressure.

7. The device of claim 6 wherein the diameter of the upper segment of the passage is sized to snugly receive a cannula or sheath therethrough.

8. The device of claim 7 wherein the deformable lip is configured to define a constriction around the bottom of the upper segment of the passage whereby said lip is capable of being deformed and pressed against a cannula or sheath when a cannula or sheath is inserted therethrough.

9. The device of claim 8 wherein the leakage cavity is in a general annular configuration around the lip.

10. The device of claim 9 wherein the leakage cavity has a curved cross-sectional configuration; said cross-section being taken along a central plane which is parallel to the passage.

11. The device of claim 6 wherein the skirt comprises an upper stem section with the upper section of the passage extending therethrough and a lower flanged section; said flanged section being wider than said stem section and said leakage cavity being located in the flanged section.

12. The device of claim 11 which further includes a torsional spring around the stem section; said spring being adapted to constrict said stem.

13. The device of claim 12 wherein the diameter of the upper segment of the passage is sized to snugly receive a cannula or sheath therethrough.

14. The device of claim 13 wherein the deformable lip is configured to define a constriction around the bottom of the upper segment of the passage whereby said lip is capable of being deformed and pressed against a cannula or sheath when a cannula or sheath is inserted therethrough.

15. The device of claim 14 wherein the leakage cavity is wider than the stem and is in a general annular configuration around the lip.

16. The device of claim 15 wherein the leakage cavity has a curved cross-sectional configuration; said cross-section being taken along a central plane which is parallel to the passage.

17. The device of claim 16 wherein the flanged section is in a general frusto conical configuration having a top surface which joins the stem section and a generally flattened bottom surface.

18. The device of claim 17 wherein the bottom surface is substantially circular.

19. The device of claim 18 wherein the top surface of the flanged section is concave.

20. The device of claim 19 wherein the bottom surface is coated with an adhesive for adhering the device to a patient's skin.

21. The device of claim 20 wherein the adhesive is a pressure sensitive adhesive and said adhesive is covered with a release strip.

22. The device of claim 21 wherein the skirt is a one-piece molded article made from flexible plastic, rubber of silicone.

23. The device of claim 22 which further comprises a slit which penetrates through the thickness of the skirt to the passage and which extends from the top to the bottom of the skirt whereby said skirt is capable of opening up to receive a cannula in the passage.

24. The device of claim 23 which further includes an adhesive overlay on the top surface of the flange; said overlay having one section which is adhered to the top surface of the flange along one side of the slit and said overlay having an adhesive flap section which is sized for adhesive contact with the flange along the other side of the slit; said adhesive flap section having a peel-away release layer over the adhesive.

25. The device of claim 11 wherein the top and bottom openings are round.

* * * * *